United States Patent
Ono (10) Patent No.: US 9,101,932 B2
(45) Date of Patent: Aug. 11, 2015

(54) FLUID HANDLING APPARATUS

(71) Applicant: Enplas Corporation, Saitama (JP)

(72) Inventor: Koichi Ono, Saitama (JP)

(73) Assignee: ENPLAS Corporation, Saitama (JP)

( * ) Notice: Subject to any disclaimer, the term of this patent is extended or adjusted under 35 U.S.C. 154(b) by 0 days.

(21) Appl. No.: 14/031,941

(22) Filed: Sep. 19, 2013

(65) Prior Publication Data

US 2014/0079602 A1 Mar. 20, 2014

(30) Foreign Application Priority Data

Sep. 20, 2012 (JP) ................................ 2012-206554

(51) Int. Cl.
| | |
|---|---|
| *B01L 3/00* | (2006.01) |
| *G01N 27/00* | (2006.01) |
| *G01N 27/447* | (2006.01) |
| *G01N 27/26* | (2006.01) |
| *G01N 33/00* | (2006.01) |

(52) U.S. Cl.
CPC .... *B01L 3/502715* (2013.01); *G01N 27/44791* (2013.01); *B01L 2200/027* (2013.01); *B01L 2200/10* (2013.01); *B01L 2300/0645* (2013.01); *B01L 2300/0816* (2013.01); *B01L 2300/0867* (2013.01); *B01L 2300/0887* (2013.01); *B01L 2300/1827* (2013.01); *B01L 2400/0415* (2013.01); *B01L 2400/0421* (2013.01)

(58) Field of Classification Search
USPC .................................................. 204/451, 601
See application file for complete search history.

(56) References Cited

U.S. PATENT DOCUMENTS

| | | | |
|---|---|---|---|
| 6,491,804 B2* | 12/2002 | Manz et al. .................... | 204/453 |
| 6,939,451 B2 | 9/2005 | Zhao et al. | |
| 2007/0102293 A1* | 5/2007 | Tai et al. ........................ | 204/409 |
| 2007/0286773 A1* | 12/2007 | Schlautmann et al. ....... | 422/68.1 |
| 2012/0118392 A1* | 5/2012 | Blankenstein et al. ........... | 137/1 |

FOREIGN PATENT DOCUMENTS

JP 2005-127771 A 5/2005

* cited by examiner

*Primary Examiner* — Jennifer Wecker
(74) *Attorney, Agent, or Firm* — Brundidge & Stanger, P.C.

(57) ABSTRACT

Microchannel chip (100) has film (120) adhered on the second surface of base (110) having a through-hole (111), and conductive layer (130). Film (120) has hole (121) and covers a second opening of the through-hole (111). Conductive layer (130) is integrally formed so as to extend from a portion of a bottom of hole (121) of base (110) to a portion of an inner surface of through-hole (111). Upon comparison with a microchannel chip in the related art, microchannel chip (100) is further reduced in size, has excellent handleability and is easy to be manufactured.

2 Claims, 11 Drawing Sheets

FLUID HANDLING APPARATUS

CROSS REFERENCE TO RELATED APPLICATIONS

This application is entitled and claims the benefit of Japanese Patent Application No. 2012-206554, filed on Sep. 20, 2012, the disclosure of which including the specification, drawings and abstract is incorporated herein by reference in its entirety.

TECHNICAL FIELD

The present invention relates to a fluid handling apparatus for performing an analysis, processing or the like of a liquid sample.

BACKGROUND ART

In recent years, in order to analyze a trace amount of a substance such as proteins or nucleic acids (DNA, for example) with high accuracy and high performance, a microanalysis system has been used in the field of science, such as biological chemistry or analytical chemistry, or in the field of medicine.

A system for performing electrophoresis using a microchannel chip having a fine channel has been known as an example of a microanalysis system. A microchannel chip in which an electrode is disposed so as to be exposed to a through-hole or a groove has been known as the microchannel chip in the system (see PTLs 1 and 2, for example). In the microchannel chip, a film formed with a conductive layer, which functions as an electrode, on a surface thereof is brought to be adhered to a first surface of a base having the through-hole for accommodating fluid, the groove functioning as a channel for the fluid and the like.

Figure 1A:
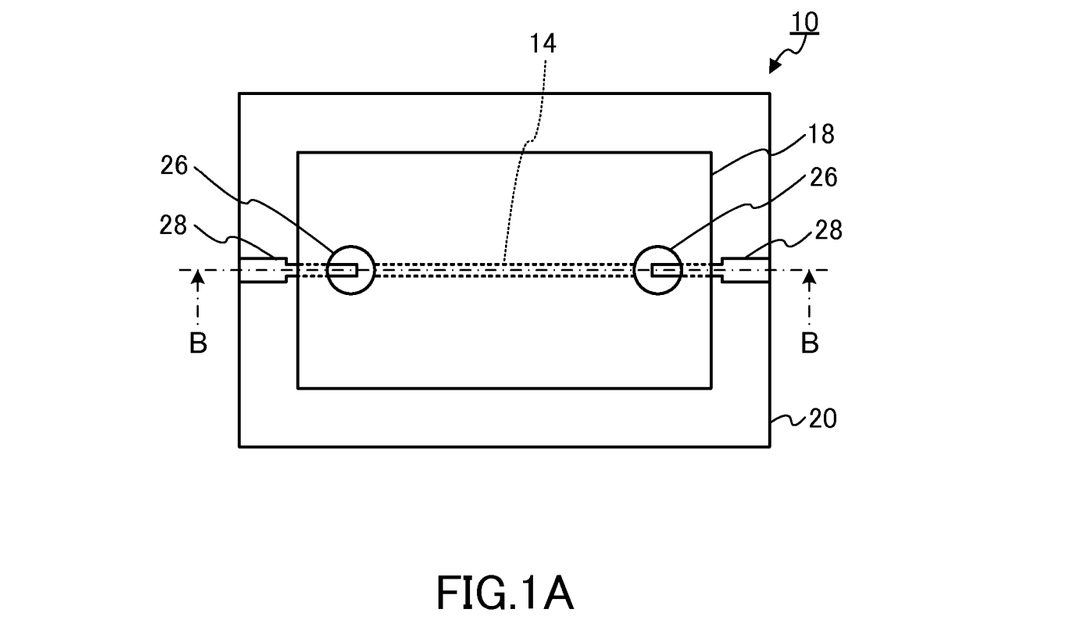
FIG. 1A is a planar view of a microchannel chip in a related art.
Figure 1B:
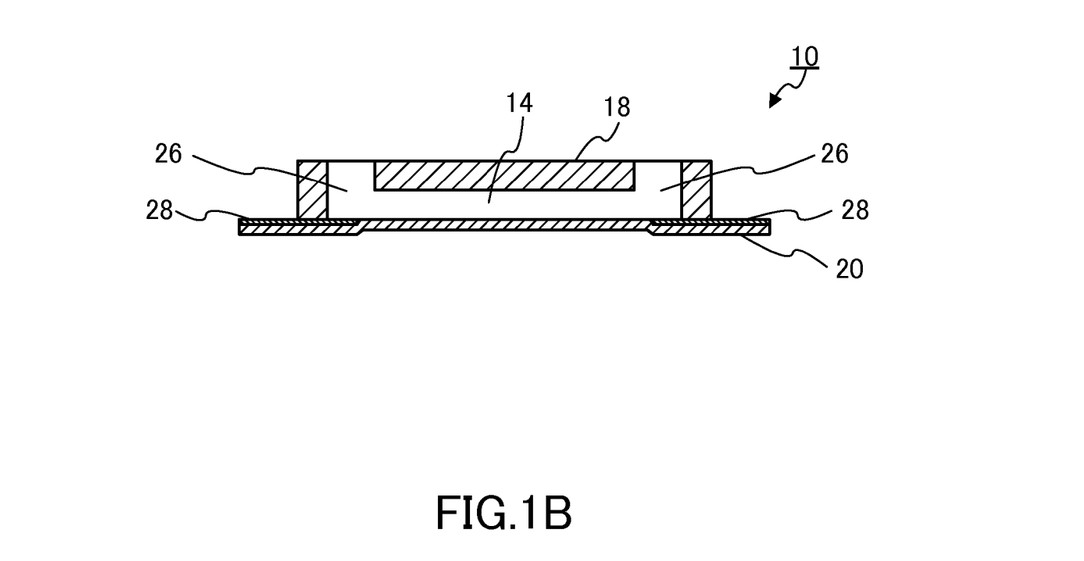
FIG. 1B is a cross-sectional view of the microchannel chip taken along a line B-B in FIG. 1A.

The microchannel chip disclosed in PTL 1 is shown in FIG. 1. Microchannel chip 10 has a pair of through-holes 26 penetrating base 18, groove 14 which is formed on a first surface of base 18 and causes the pair of through-holes 26 to communicate with each other, film 20 which is brought to be adhered to the first surface of base 18 and covers openings of through-hole 26 and groove 14, electrode 28 which is formed on film 20, is exposed to through-hole 26 and extends at least to a peripheral edge of film 20, as shown in FIG. 1. By bringing film 20 to be adhered to base 18, through-hole 26 functions as a fluid container, and groove 14 functions as a channel. A liquid sample is supplied to through-hole 26 from an upper surface side of base 18. In addition, film 20 has an edge protruding further outside than an edge of base 18. External electrodes are respectively in contact with electrodes 28 and 28 on the edge of film 20 from above, and thereby voltage is applied to electrodes 28 and 28.

CITATION LIST

Patent Literature

PTL 1
U.S. Pat. No. 6,939,451
PTL 2
Japanese Patent Application Laid-Open No. 2005-127771

SUMMARY OF INVENTION

Technical Problem

In the case of microchannel chip 10 in the above related art, it is necessary to set the size of film 20 to be bigger than that of base 18. Therefore, it is difficult for microchannel chip 10 to be reduced in size. In addition, since both an operation for supplying a liquid sample and an operation for applying voltage are performed from an upper surface side of base 18, there is also a problem in that an external device for supplying a liquid sample easily hinders an external device for supplying an electric power. In order to prevent such a hindrance, it is necessary to manufacture a microchannel chip having an enough size or to precisely operate the external devices so as not to cause a hindrance therebetween. As described above, it is difficult for microchannel chip 10 in the related art to be reduced in size and to be handled when it is used.

As means for solving the problems described above, it is considerable to cause an electrode to be exposed to a rear surface of a microchannel chip. To expose the electrode to the rear surface, it is necessary to form a hole on a film. If the electrode is formed on the film (a surface adhering to the base) as in the conventional case, it is necessary to form at least a part of the electrode, which is to be exposed from the hole of the film, on the base. In other words, it is necessary to precisely form conductive parts, which function as an electrode, on both of the base and the film such that both conductive parts form a single electrode when the film is brought to be adhered to the base. However, it is very difficult to form the electrodes on the microchannel chip as precisely as described above.

An object of the present invention is to provide a fluid handling apparatus that is further reduced in size, has excellent handleability and is easy to be manufactured.

Solution to Problem

To achieve the object described above, there is provided a fluid handling apparatus according to the present invention. The fluid handling apparatus according to the present invention has a base which has a first surface, a second surface opposing to the first surface, and a through-hole penetrating the base and having a first opening formed on the first surface and a second surface formed on the second surface, a film adhered to the second surface to cover the second opening, the film having a hole at a position apart from the second opening in a planar direction of the base, and a transfer function layer for transferring heat or electrical conduction, the transfer function layer being disposed on the base so as to connect a portion in the second surface, the portion being exposed from the hole, and a portion of an inner surface of the through-hole.

Advantageous Effects of Invention

According to the present invention, it is possible to supply fluid to a recess portion, which is formed by the through-hole and the film adhering on the second surface of the base, from the first surface side of the base. Further, it is possible to connect an electric power source or a heat source to the transfer function layer, from the second surface side of the base. Therefore, it is possible for the fluid handling apparatus to be further reduced in size. In addition, since a device for supplying fluid to a fluid container and a device for supplying energy to the transfer function layer are not disposed alternately on the same side, it is unnecessary to prepare a countermeasure for preventing a hindrance from occurring between the devices. Therefore, it is possible to provide a fluid handling apparatus having excellent handleability. Furthermore, since the transfer function layer is formed at a predetermined position on the second surface side of the base, it is possible to form the transfer function layer which is exposed to the second surface side of the base. Thus, it is easy to manufacture the fluid handling apparatus.

DESCRIPTION OF EMBODIMENTS

Hereinafter, embodiments of the present invention will be described in detail, with reference to drawings. In the following description, a microchannel chip capable of performing electrophoresis will be described as a representative example of a fluid handling apparatus according to the present invention.

Embodiment 1

Configuration of Microchannel Chip

Figure 2A:
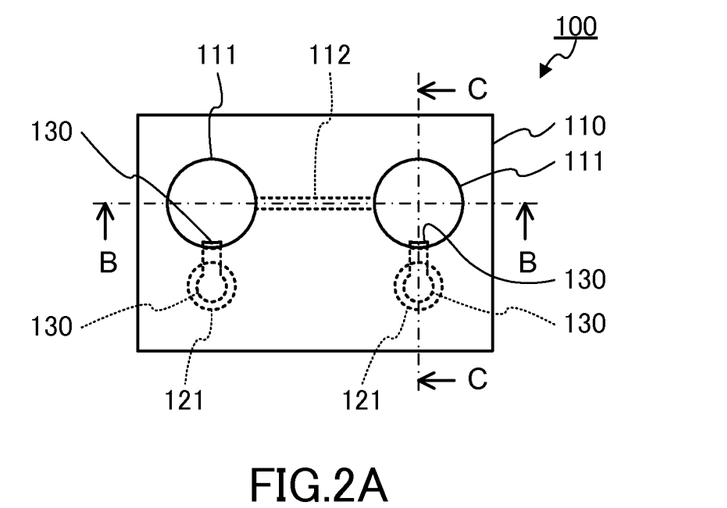
FIG. 2A is a planar view of a fluid handling apparatus according to an embodiment 1 of the present invention.
Figure 2B:
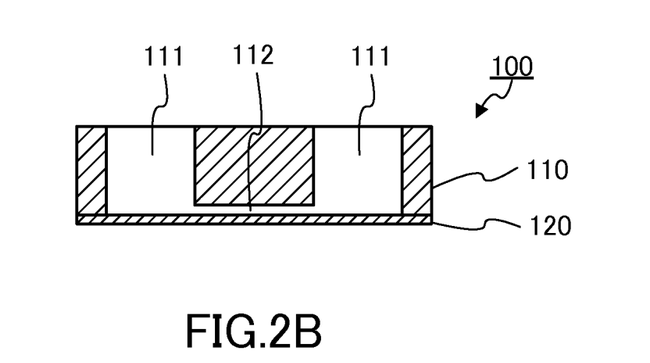
FIG. 2B is a cross-sectional view of the fluid handling apparatus taken along a line B-B in FIG. 2A.
Figure 2C:
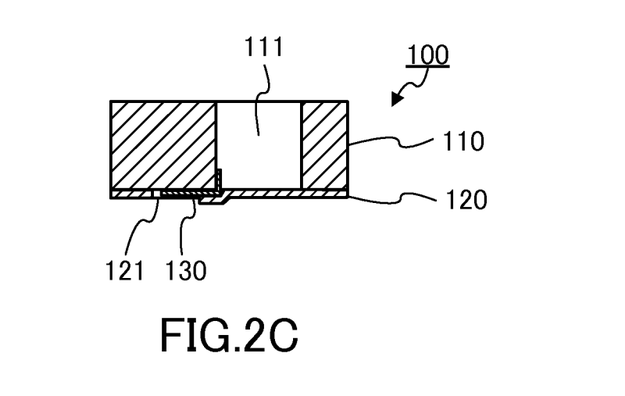
FIG. 2C is a cross-sectional view of the fluid handling apparatus taken along a line C-C in FIG. 2A.

FIG. 2 is a view showing a configuration of microchannel chip 100 according to an embodiment 1 of the present invention. FIG. 2A is a planar view of microchannel chip 100, FIG. 2B is a cross-sectional view of microchannel chip 100 taken along a line B-B in FIG. 2A, and FIG. 2C is a cross-sectional view of microchannel chip 100 taken along a line C-C of FIG. 2A.

As shown in FIGS. 2A to 2C, microchannel chip 100 has base 110, film 120 and conductive layer 130.

Figure 3A:
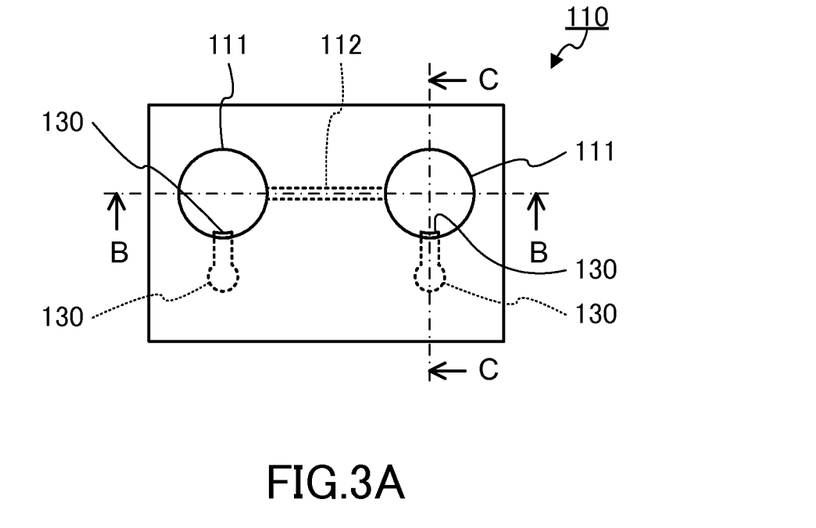
FIG. 3A is a planar view of a base of the fluid handling apparatus according to the embodiment 1 of the present invention.
Figure 3B:
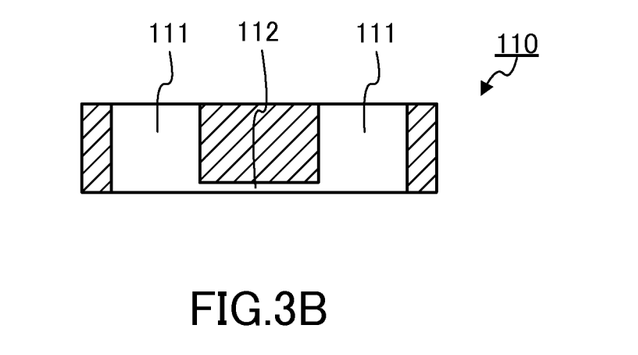
FIG. 3B is a cross-sectional view of the base taken along a line B-B in FIG. 3A.
Figure 3C:
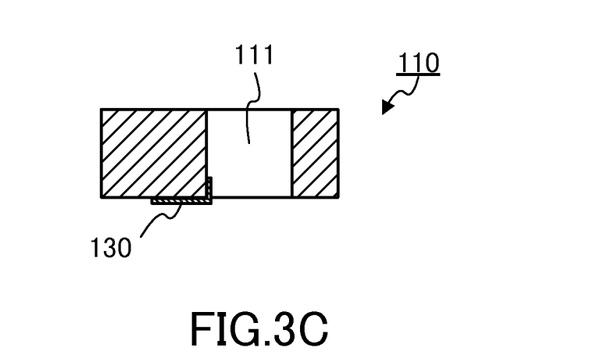
FIG. 3C is a cross-sectional view of the base taken along a line C-C in FIG. 3A.

FIG. 3 is a view showing a configuration of base 110. FIG. 3A is a planar view of base 110, FIG. 3B is a cross-sectional view of base 110 taken along a line B-B in FIG. 3A, and FIG. 3C is a cross-sectional view of base 110 taken along a line C-C in FIG. 3A.

Base 110 is a resin plate having transparency and a rectangular shape, for example. Although the thickness of base 110 is not particularly limited, it is from 1 to 10 mm, for example. Although the type of the resin constituting base 110 is not particularly limited, it can be appropriately selected from known resins depending on a purpose of microchannel chip 100. Polyethylene terephthalate, polycarbonate, polymethyl methacrylate, vinyl chloride, polypropylene, polyether, polyethylene or the like is included as an example of the resin constituting base 110.

Base 110 has two a through-hole 111 and 111, and groove 112 which causes two through-holes 111 and 111 to communicate with each other. Through-hole 111 has a first opening formed on a first surface (an upper surface) and a second opening formed on a second surface (a lower surface) of base 110. Each of the first opening and the second opening of through-hole 111 has a circular shape, for example. Although the diameter of through-hole 111 is not particularly limited, it is about 6 mm, for example. Groove 112 is formed on the second surface of the base 110. Groove 112 has an approximately rectangular cross-sectional shape, for example. Although groove 112 is not particularly limited in width and depth, it is about 1 mm in width and about 0.5 mm in depth, for example.

Figure 4A:
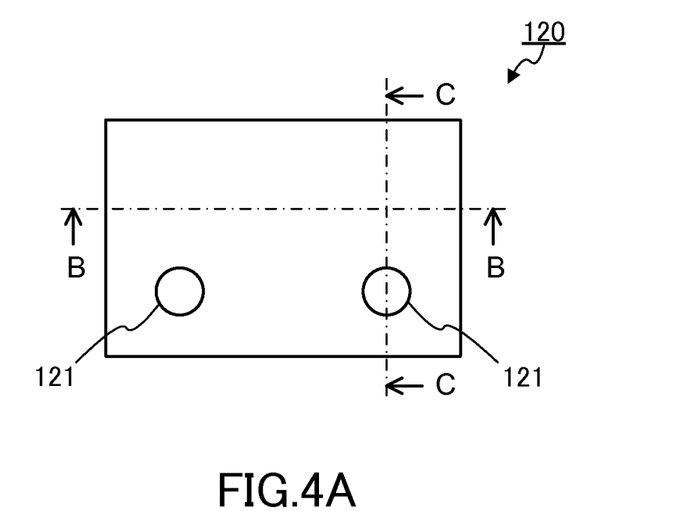
FIG. 4A is a planar view of a film of the fluid handling apparatus according to the embodiment 1 of the present invention.
Figures 4B, 4C:
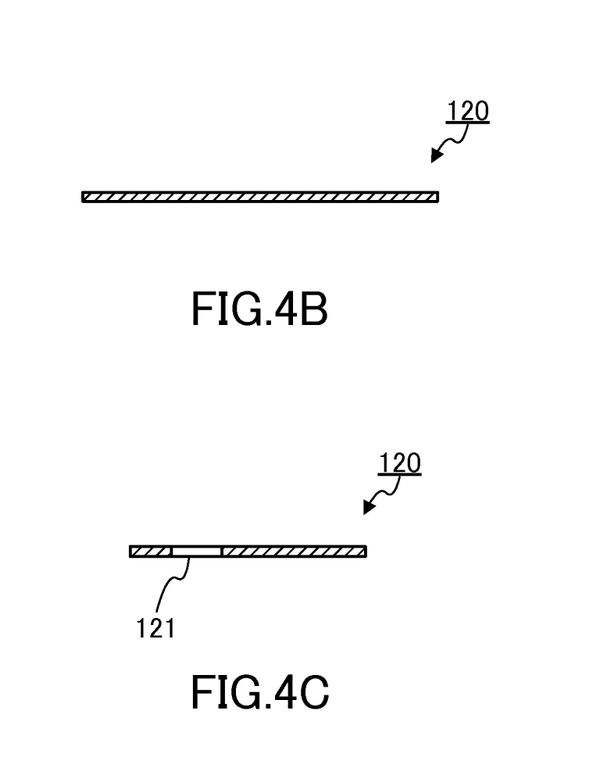
FIG. 4B is a cross-sectional view of the film taken along a line B-B in FIG. 4A.
FIG. 4C is a cross-sectional view of the film taken along a line C-C in FIG. 4A.

FIG. 4 is a view showing a configuration of film 120. FIG. 4A is a planar view of film 120, FIG. 4B is a cross-sectional view of film 120 taken along a line B-B in FIG. 4A, and FIG. 4C is a cross-sectional view of film 120 taken along a line C-C in FIG. 4A.

Film 120 is a resin film having transparency and a rectangular shape, for example. Although the type of the resin constituting film 120 is not particularly limited, it can be appropriately selected from known resins depending on a purpose of microchannel chip 100. An example of the resin constituting film 120 is the same as that of the resin constituting base 110. From the point of view of improving adhesion between base 110 and film 120, it is preferable that film 120 be constituted by the same resin as that of base 110.

An external shape of film 120 in planar view is the same as that of base 110. Although the thickness of film 120 is not particularly limited, it is about 100 μm, for example. Film 120 has holes 121 and 121. Hole 121 is positioned apart from the second opening of through-hole 111 on the second surface, in a planar direction of substrate 110 and a direction perpendicular to a longitudinal direction of groove 112. Although the shape of hole 121 is not particularly limited, it is a circular shape, for example. Although the diameter of hole 121 is not particularly limited, it is about 3 mm, for example. Although the distance between hole 121 and through-hole 111 is not particularly limited, the shortest distance therebetween is about 1 mm in planar view, for example.

Conductive layer 130 is a layer having conductivity. Conductive layer 130 is a metallic thin film, for example. Conductive layer 130 may be a layer of a composition in which conductive filler such as metal powder and graphite powder is dispersed. Although the thickness of conductive layer 130 is not particularly limited, it is about 10 μm, for example. As shown in FIGS. 2 and 3, conductive layer 130 is formed on the second surface of base 110. More specifically, when film 120 is brought to be adhered to the second surface of base 110, conductive layer 130 is formed so as to extend from a portion on base 110, which is exposed from hole 121, to an end portion (a lower end portion) of the inner surface of through-hole 111, which is on the second surface side of the base 110, in a state where the film 120 is adhered to the second surface of base 110. One end of conductive layer 130 is exposed from hole 121, and the other end of the conductive layer 130 is exposed at a lower end portion of the inner surface of through-hole 111. The shape of conductive layer 130 is not particularly limited. One end portion of conductive layer 130 has an approximately circular shape, for example. The other end portion of conductive layer 130 has an approximately rectangular shape, for example. Although the exposed area of the other end of the conductive layer 130 is not particularly limited with respect to through-hole 111, it is about 1 mm$^2$, for example.

Microchannel chip 100 is obtained by the following manner. First, base 110 having through-hole 111 and groove 112 is prepared, and then conductive layer 130 is formed on the second surface of base 110. Next, film 120 is brought to be adhered to the second surface of base 110. Through-hole 111 and groove 112 may be formed on base 110 in a known manner. Conductive layer 130 may be formed in a known manner such as adhesion of metallic thin film, deposition of metal or coating of a conductive paste. It is possible to form entire conductive layer 130 at once. Also, it is possible to partially and successively form conductive layer 130. Film 120 may be adhered to the second surface of base 110 in a known manner such as thermocompression bonding.

The second opening of through-hole 111 on the second surface side of base 110 is covered with film 120, and thereby through-hole 111 constitutes a bottomed recess portion (also, referred to as a "reservoir") for accommodating fluid, as shown in FIG. 2. An opening of groove 112 is covered with film 120, thereby constituting a passage (also, referred to as a "channel") for communicating with the reservoir. Film 120 is brought to be adhered to the second surface of base 110, thereby conductive layer 130 is disposed between base 110 and film 120.

Next, a method using microchannel chip 100 for performing electrophoresis of a liquid sample will be described as an example of an application method of microchannel chip 100. First, electrolytes and a liquid sample are injected into the reservoir, form the first surface side of base 110 so that the reservoir and the channel are filled with the electrolytes and the liquid sample. Subsequently, an external electrode bar is brought into contact with one end portion of conductive layer 130 which is exposed on the second surface side of base 110, from the second surface side of base 110. Then, voltage is applied to conductive layers 130 and 130. By applying voltage, electrophoresis occurs in the channel. Results of electrophoresis can be obtained immediately by measuring the fluorescence intensity at the predetermined position in the channel.

[Effect]

In microchannel chip 100, fluid can be supplied from the first surface side of base 110, and electric power can be supplied to conductive layer 130 from the second surface side of base 110. Therefore, it is not necessary to extend conductive layer 130 to an outer edge portion of the microchannel chip. Thus, upon comparison with a microchannel chip of the related art in which a conductive layer is exposed to the outer edge portion of base 110, it is possible for the microchannel chip to be further reduced in size. In addition, since it is not necessary to dispose a device for supplying fluid to microchannel chip 100 and a device for supplying an electric power, next to each other or one by one, it is not necessary to consider a disposition or an operation for preventing a hindrance from occurring between both devices. Therefore, it is possible for microchannel chip 100 to have excellent handleability even when being reduced in size. Furthermore, it is possible to form conductive layer 130 to which an external electric power source can be connected from the second surface side of base 110, by only integrally forming conductive layer 130 on the second surface of base 110. Therefore, since it is not necessary to precisely form conductive parts, which function as conductive layer 130, on both of base 110 and film 120, it is possible to easily manufacture microchannel chip 100. Furthermore, conductive layer 130 formed in microchannel chip 100 is backed on base 110. Therefore, it is possible to further improve a contact property of conductive layer 130 to an external electrode.

Figure 5A:
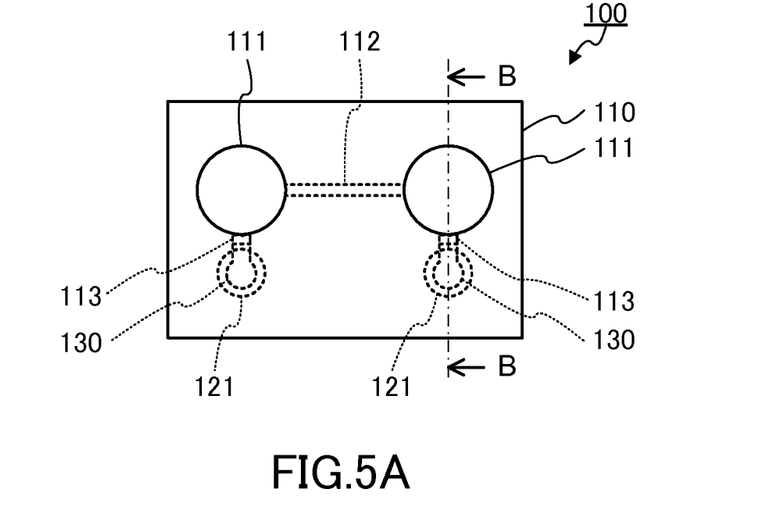
FIG. 5A is a planar view of a partially modified example of the fluid handling apparatus according to the embodiment 1 of the present invention.
Figure 5B:
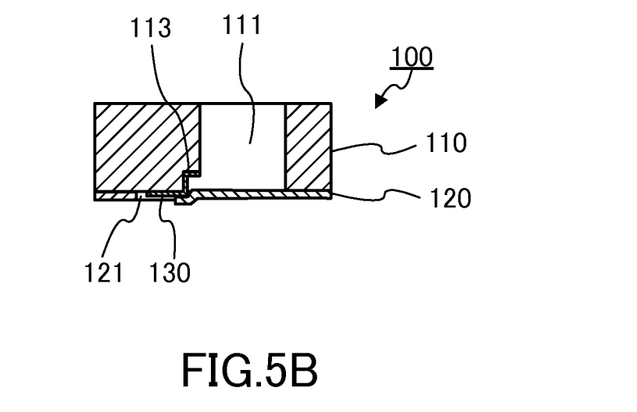
FIG. 5B is a cross-sectional view of the modification example taken along a line B-B in FIG. 5A.

In addition, a notch portion may be additionally formed in base 110 by the second opening of through-hole 111 in the second surface of base 110. For example, as shown in FIGS. 5A and 5B, a step-shaped notch portion 113 may be formed on a part of the edge of the second opening of through-hole 111 on the second surface side. In this case, conductive layer 130 is formed on a step-shaped wall surface formed by notch portion 113. Thereby, since a contact area of conductive layer 130 and the fluid in through-hole 111 is further increased, it is possible to further reduce partial-current concentration in the fluid in through-hole 111.

Embodiment 2

Configuration of Microchannel Chip

Figure 6A:
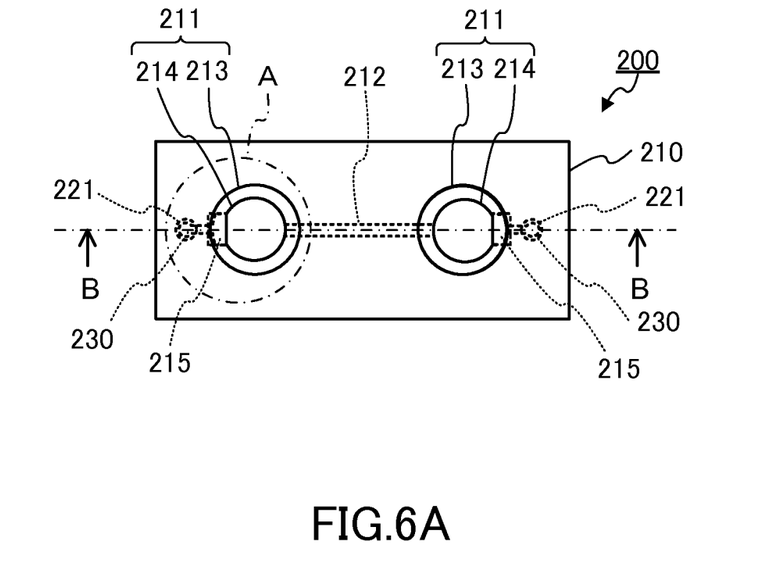
FIG. 6A is a planar view of a fluid handling apparatus according to an embodiment 2 of the present invention.
Figure 6B:
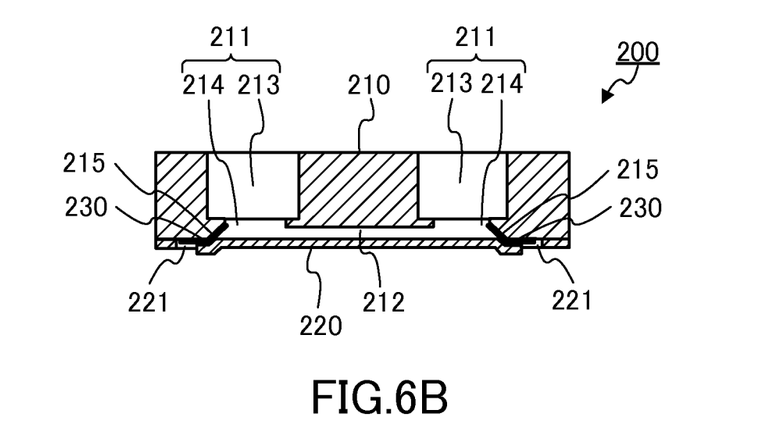
FIG. 6B is a cross-sectional view of the fluid handling apparatus taken along a line B-B in FIG. 6A.

FIG. 6 is a view showing a configuration of microchannel chip 200 according to an embodiment 2 of the present invention. FIG. 6A is a planar view of microchannel chip 200, and FIG. 6B is a cross-sectional view of microchannel chip 200 taken along a line B-B in FIG. 6A.

As shown in FIG. 6, microchannel chip 200 has base 210, film 220 and conductive layer 230.

Figure 7A:
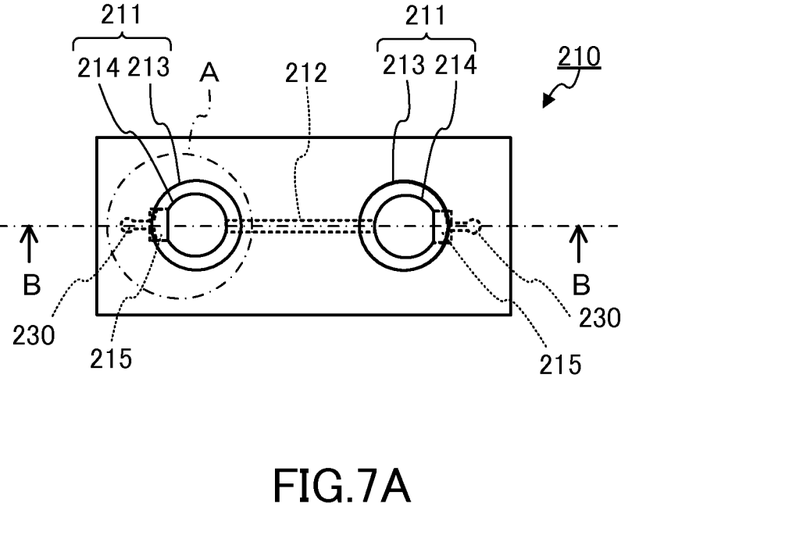
FIG. 7A is a planar view of a base of the fluid handling apparatus according to the embodiment 2 of the present invention.
Figure 7B:
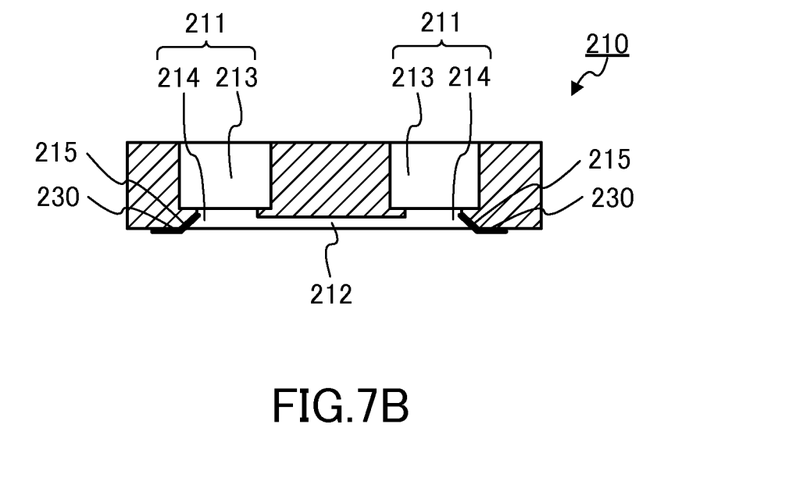
FIG. 7B is a cross-sectional view of the base taken along a line B-B in FIG. 7A.

FIG. 7A is a planar view of base 210, and FIG. 7B is a cross-sectional view of base 210 taken along a line B-B in FIG. 7A.

Base 210 has two through-holes 211 and 211, and groove 212 which causes two through-holes 211 and 211 to communicate with each other. A material and a thickness of base 210 is the same as that of base 110, for example.

Through-hole 211 includes a recess portion 213 which is opened in a first surface of base 210 and has a bottom surface, and a first communication hole 214 which penetrates the bottom of recess portion 213 and functions as the hole mentioned above for causing recess portion 213 and the second surface of base 210 to communicate with each other and further causing recess portion 213 and groove 212 to communicate with each other. An inner wall surface of first communication hole 214 includes inclined surface 215 formed on the second opening on the second surface side of the base 210. The inner wall surface of first communication hole 214 includes a wall surface which extends from an opening on the recess portion 213 side so as to be perpendicular to the bottom surface of recess portion 213. Groove 212 is opened to the wall surface. The shape and size of the opening of recess portion 213, which is on the first surface of base 210, is the same as those of the first opening of through-hole 111, for example.

In the present invention, a "through-hole" means a space which is formed in the base, has openings on both surfaces of a base, and causes the first surface and the second surface of the base to communicate with each other. The shape of a through-hole is not particularly limited. The through-hole may be constituted by a single hole, as the case of through-hole 111. Alternatively, the through-hole may be constituted by connecting a recess portion, a hole and the like, as the case of through-hole 211, as well.

The cross-sectional shape and the size of groove 212 are the same as those of groove 112, for example.

In the bottom of recess portion 213, an opening of first communication hole 214 has a bow shape that is surrounded by an arc which is about a five-sixth circumference of a circle having a diameter smaller than an outside dimension of the bottom surface of recess portion 213 and a straight line (a chord) connecting both ends of the arc. In the second surface of base 210, the second opening of first communication hole 214 has a shape which is constituted by joining a rectangular shape to the chord by the second opening of first communication hole 214 in planar view. Inclined surface 215 is formed so as to be inclined from a long side of the rectangular shape of the second opening of first communication hole 214 on the second surface side toward a wall surface of first communication hole 214 on the chord side in the bow-shaped opening shape of first communication hole 214, which is on the bottom side of recess portion 213.

Figure 8A:
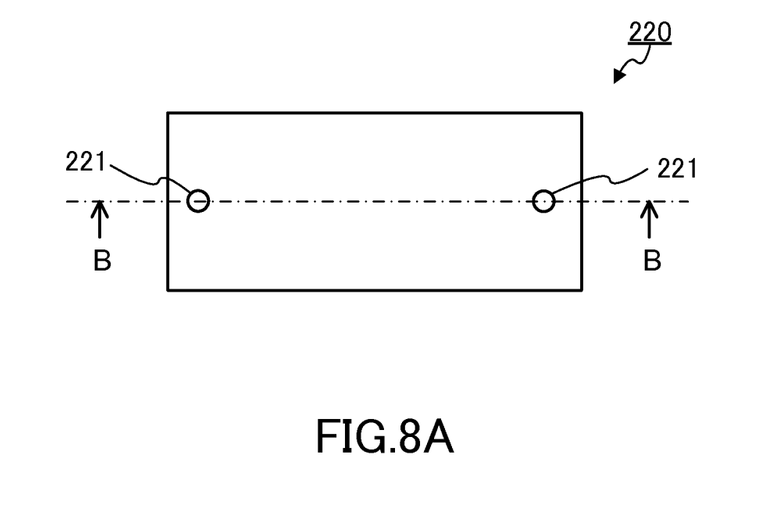
FIG. 8A is a planar view of a film of the fluid handling apparatus according to the embodiment 2 of the present invention.
Figure 8B:
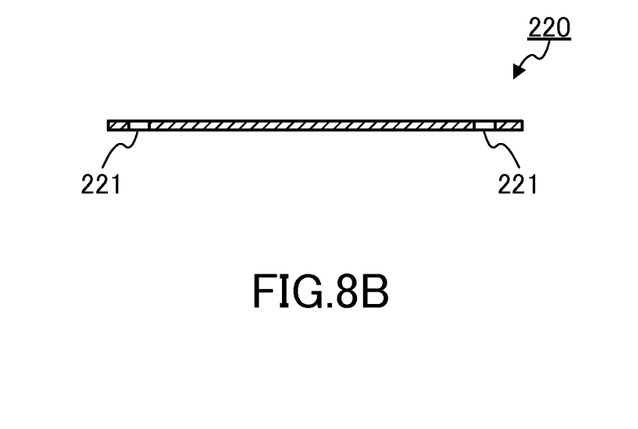
FIG. 8B is a cross-sectional view of the film taken along a line B-B in FIG. 8A.

FIG. 8A is a planar view of film 220, and FIG. 8B is a cross-sectional view of film 220 taken along a line B-B in FIG. 8A.

Film 220 has two holes 221. Holes 221 are respectively disposed on end portion sides of base 210 in a longitudinal direction of groove 212, in a planar direction of base 210. It is possible for film 220 to have the same configuration as that of film 120, except for the disposition of hole 221.

Conductive layer 230 is a layer formed by drying and hardening a coating film of a conductive paste, for example. When film 220 is brought to be adhered to the second surface of base 210, conductive later 230 is formed so as to extend from a portion on base 210, which is exposed from hole 221, to a portion of inclined surface 215 (see FIGS. 6, 7 and 9). One end portion of conductive layer 230 which is exposed from hole 221 is formed in a substantially circular shape. The other end portion of conductive layer 230, which is on the inclined surface 215, is formed in a substantially bow shape that spreads from the hole 221 side toward the chord side in the bow-shaped opening shape of first communication hole 214, which is on the bottom surface side of recess portion 213, for example. A "bow shape" is a shape surrounded by an arc and a chord (a straight line) connecting both ends thereof. Although the exposed area of conductive layer 230 in inclining surface 215 is not particularly limited, it is about 3 mm$^2$, for example.

As similar to the case of microchannel chip 100, microchannel chip 200 is obtained by a following manner. First, base 210 is prepared, and then conductive layer 230 is formed on the second surface of base 210. Next, film 220 is brought to be adhered to the second surface of base 210. It is possible to form recess portion 213, first communication hole 214 and groove 212 on base 210 in the known manner. Conductive layer 230 can be formed in a known manner such as a screen printing used to apply a conductive paste or the like. It is possible to bring film 220 to be adhered to the second surface of base 210 in a known manner such as a thermocompression bonding.

Figure 9A:
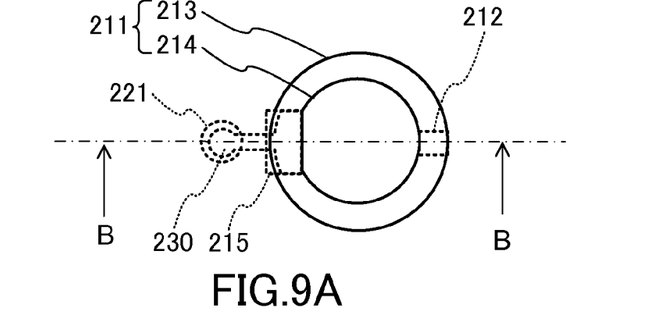
FIG. 9A is an enlarged view of a part A of the fluid handling apparatus shown in FIG. 6A.
Figure 9B:
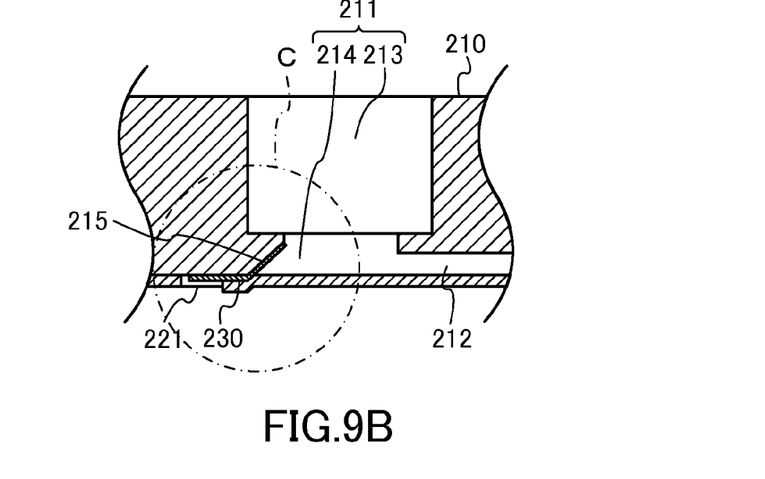
FIG. 9B is a cross-sectional view of the same part taken along a line B-B in FIG. 9A.
Figure 9C:
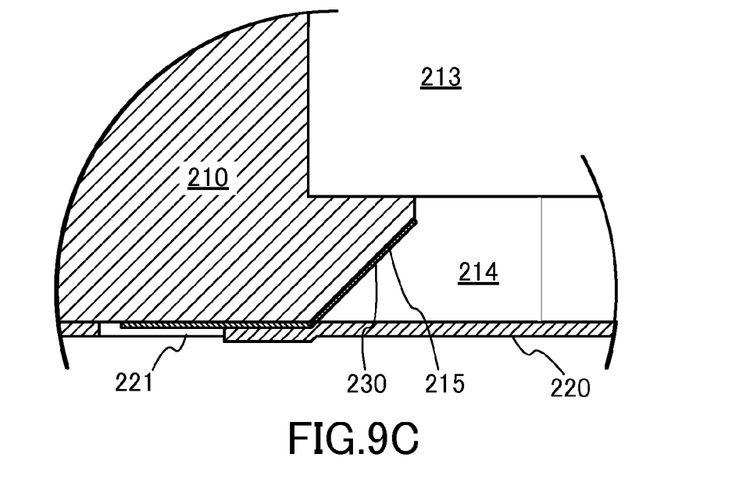
FIG. 9C is an enlarged view of part C shown in FIG. 9B.

FIG. 9A is an enlarged view of a portion A shown in FIG. 6A, FIG. 9B is a cross-sectional view of the same part taken along a line B-B in FIG. 9A, and FIG. 9C is an enlarged view of a part C shown in FIG. 9B.

By covering the second opening on the second surface side of base 210 with film 220, a bottomed recess portion for accommodating fluid, which is constituted by a recess portion 213 and first communication hole 214, is formed, as shown in FIGS. 6 and 9. In this case, recess portion 213 is a reservoir for accommodating fluid which is supplied when using microchannel chip 200. First communication hole 214 is a space for accommodating the fluid to transfer an electric power to the fluid in the reservoir. By covering the opening of groove 212 with film 220, groove 212 constitutes a passage to cause the reservoirs to communicate with each other. By bringing film 220 to be adhered to base 210, inclined surface 215 forms a surface which is inclined from the second surface of base 210 to the wall surface of first communication hole 214. In inclined surface 215, a distance between film 220 and inclined surface 215 in a thickness direction of base 210 gradually increases with increasing a distance between an outer edge of first communication hole 214, which is on the hole 221 side, and the chord of the bow-shaped opening shape of the opening of recess portion 213, which is on the bottom surface side, in the planar direction of base 210. Thus, inclined surface 215 is inclined from the second surface of base 210 to the inner surface of through-hole 211, such that a distance between film 220 and inclined surface 215 in a thickness direction of base 210 gradually increases as inclined surface 215 approaches to through-hole 211 from hole 221 side in the planar direction of base 210. By bringing film 220 to be adhered to the second surface of base 210, conductive layer 230 is disposed between base 210 and film 220. One end portion of conductive layer 230 is exposed to the second surface side of base 210, from hole 221. As similarly to the case of microchannel chip 100, microchannel chip 200 can be used to perform electrophoresis.

[Effect]

Microchannel chip 200 achieves the following effects, in addition to the effects achieved in the case of microchannel chip 100. Microchannel chip 200 has inclined surface 215 extending from the second surface of base 210. Conductive layer 230 is formed over almost the entire inclined surface 215. Therefore, since the contact area of conductive layer 230 and the fluid in the fluid container (reservoir) is more increased, it is possible to further reduce current concentration in the fluid. Furthermore, in base 210, a part at which conductive layer 230 is formed, including inclined surface 215, faces the second surface side of base 210 in a thickness direction of base 210. Thus, it is possible to form one or more conductive layers 230 all at once by the screen printing method or the like which enables conductive layer 230 to be formed from the second surface side of base 210. Therefore, microchannel chip 200 is better than microchannel chip 100, in terms of productivity.

Figure 10:
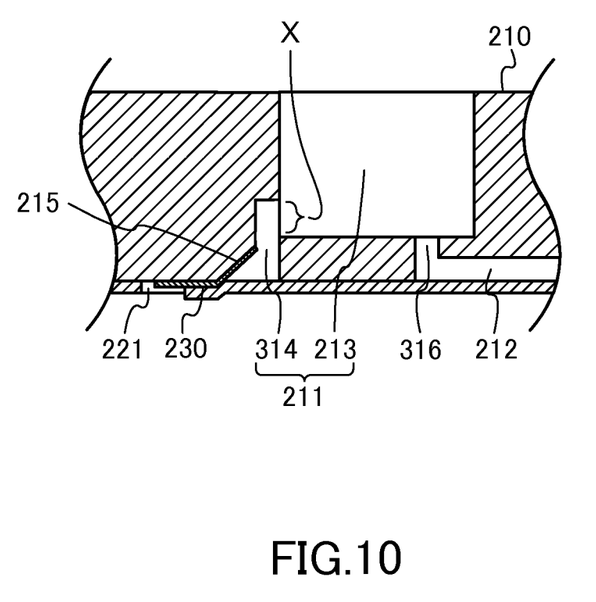
FIG. 10 is a cross-sectional view of a partially modified example of the fluid handling apparatus according to the embodiment 2 of the present invention.

Furthermore, the position of first communication hole 214 in planar view of base 210 is not limited to the position to be superimposed on recess portion 213. For example, a first communication hole may be located at the position to be in contact with a side wall of recess portion 213 in planar view, as shown by a reference numeral 314 in FIG. 10. In this case, an opening which causes recess portion 213 and first communication hole 314 to communicate with each other is formed at a position (an X portion in FIG. 10) where the side wall of first communication hole 314 is superimposed on a side wall of recess portion 213 in a thickness direction of base 210. In addition, it is possible to individually provide first communication hole 314 and second communication hole 316 which causes recess portion 213 and groove 212 to communicate with each other. Even in such a structure, it is possible to obtain the same effects as those of microchannel chip 200. Furthermore, the shapes of first communication holes 214 and 314 are not limited to those shown in the embodiments described above. For example, first communication holes 214 and 314 are formed so as to be opened on both the bottom surface of recess portion 213 and the second surface of base 210. Further, at least a part of the opening edge on the second surface of base 210, which is located near hole 221 of film 220, may be chamfered. By forming conductive layer 230 so as to extend from a portion of the chamfered portion to a portion exposed from hole 221 of film 220, it is possible to obtain the same effects as those of the embodiments described above.

Modification Example

Figure 11A:
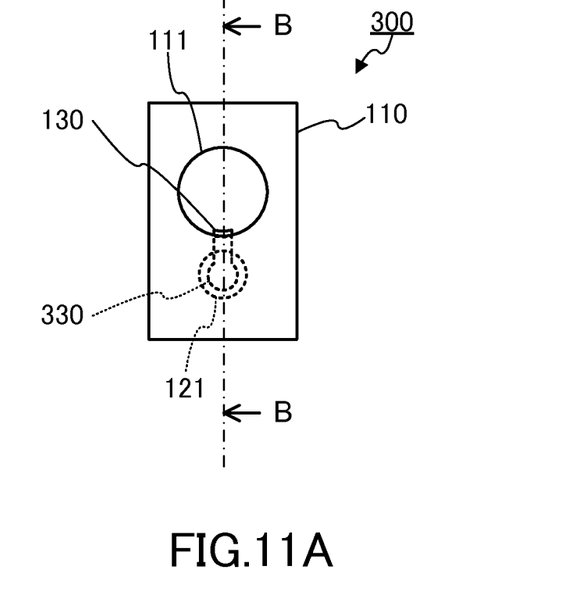
FIG. 11A is a planar view of a fluid handling apparatus according to another embodiment of the present invention.
Figure 11B:
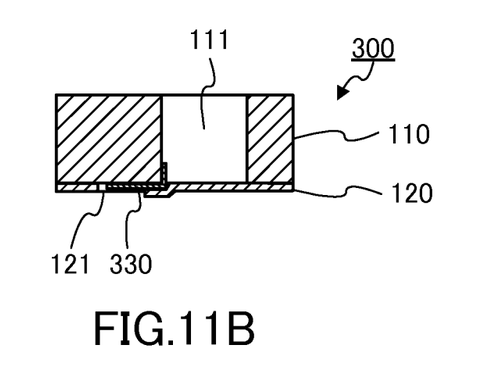
FIG. 11B is a cross-sectional view of the fluid handling apparatus taken along a line B-B in FIG. 11A.

Although the embodiments of the present invention are described referring to a microchannel chip for performing electrophoresis, as an example, the fluid handling apparatus according to the present invention is not limited to a microchannel chip for performing electrophoresis. For example, the fluid handling apparatus according to the present invention may be microchannel chip 300 which regulates the temperature of fluid by adopting heat transfer layer 330 instead of conductive layer 130, as shown in FIG. 11. Heat transfer layer 330 may be made of a known material having a heat transfer property so as to have the same configuration as that of conductive layer 130. In a state of being in contact with heat transfer layer 330 from the second surface side of base 110, a heat source of heat transfer layer 330 supplies heat or cold to heat transfer layer 330. In microchannel chip 300, it is possible to immediately obtain the heat treatment result of fluid by measuring the optical properties, such as turbidity, of a liquid sample in a reservoir.

INDUSTRIAL APPLICABILITY

A fluid handling apparatus according to the present invention is useful as a microchannel chip used in the field of science, medicine or the like.

REFERENCE SIGNS LIST 10, 100, 200, 300 Microchannel chip
14, 112, 212 Groove
18, 110, 210 Base
20, 120, 220 Film
26, 111, 211 Through-hole
28 Electrode
113 Notch portion
121, 221 Hole
130, 230 Conductive layer
211 First recess portion
213 Recess portion
214, 314 First communication hole
215 Inclined surface
316 Second communication hole
330 Heat transfer layer

The invention claimed is:

1. A fluid handling apparatus comprising:
a base which has a first surface, a second surface opposing to the first surface, and a through-hole penetrating the base and having a first opening formed on the first surface and a second opening formed on the second surface;
a film adhered to the second surface to cover the second opening, the film having a through-hole at a position apart from the second opening in a planar direction of the base; and
a transfer function layer for transferring heat or electrical conduction, the transfer function layer disposed in the through hole of the film and extending into the through-hole of the base.

2. The fluid handling apparatus according to claim 1, wherein the base further includes an inclined surface which is inclined from the second surface to an inner surface of the through-hole of the base, such that a distance between the film and the inclined surface in a thickness direction of the base gradually increases as the inclined surface approaches to the through-hole of the base from the through-hole of the film side in the planar direction of the base.

* * * * *